US008664196B2

(12) United States Patent
Valoti et al.

(10) Patent No.: US 8,664,196 B2
(45) Date of Patent: Mar. 4, 2014

(54) SHARK-LIKE CHONDROITIN SULPHATE AND PROCESS FOR THE PREPARATION THEREOF

(75) Inventors: Ermanno Valoti, Milan (IT); Niccolò Miraglia, Desio (IT); Davide Bianchi, Desio (IT); Marco Valetti, Desio (IT); Paola Bazza, Desio (IT)

(73) Assignee: Gnosis S.p.A., Desio (MB) (IT)

( * ) Notice: Subject to any disclaimer, the term of this patent is extended or adjusted under 35 U.S.C. 154(b) by 224 days.

(21) Appl. No.: 13/112,696

(22) Filed: May 20, 2011

(65) Prior Publication Data

US 2012/0295865 A1    Nov. 22, 2012

(51) Int. Cl.
*A61K 31/715*    (2006.01)
*C07H 5/04*    (2006.01)
*C07H 5/06*    (2006.01)

(52) U.S. Cl.
USPC .......................... 514/53; 536/18.7; 536/55.3

(58) Field of Classification Search
USPC .................................. 536/18.7, 55.3; 514/53
See application file for complete search history.

(56) References Cited

U.S. PATENT DOCUMENTS

| 6,288,044 | B1 | 9/2001 | Zoppetti et al. |
| 6,777,398 | B2 | 8/2004 | Zoppetti et al. |
| 2009/0233336 | A1 | 9/2009 | Sugiura et al. |
| 2009/0263867 | A1 | 10/2009 | Sugiura et al. |
| 2010/0063001 | A1 | 3/2010 | Jolly et al. |
| 2010/0151532 | A1 | 6/2010 | Suzuki et al. |
| 2012/0010399 | A1 | 1/2012 | Trilli et al. |
| 2012/0135470 | A1 | 5/2012 | De Rosa et al. |

FOREIGN PATENT DOCUMENTS

EP    1270599 B1 *  3/2004

OTHER PUBLICATIONS

Manzoni, M. et al., Production and Purification of an Extracellularly Produced K4 Polysaccharide From *Escherichia coli*, Biotechnology Letters, 1996, 383-386, vol. 18, Issue 4.
Rodriguez, Maria-Luisa et al., Structure and Serological Characteristics of the Capsular K4 Antigen of *Escherichia coli* O5:K4:H4, a Fructose-Containing Polysaccharide with a Chondroitin Backbone, European Journal of Biochemistry, 1988, 117-124, vol. 177.
Sim, Joon-Soo et al., Quantitative Analysis of Chondroitin Sulfate in Raw Materials, Ophthalmic Solutions, Soft Capsules and Liquid Preparations, Journal of Chromatography B, 2005, 133-139, vol. 818, Elsevier B.V.
Fukuta, M. et al., "Molecular cloning and expression of chick chondrocyte chondroitin 6-sulfotransferase," J. of Biological Chemistry, vol. 270, No. 31, 1995, pp. 18575-18580.
Kitagawa, H. et al., "Molecular cloning and expression of novel chondroitin 6-O-sulfotransferase," J. of Biological Chemistry, vol. 275, No. 28, 2000, pp. 21075-21080.
Schiraldi, C. et al., "Purification of chondroitin precursor from *Escherichia coli* K4 fermentation broth using membrane processing," Biotechnology Journal, vol. 6, No. 4, 2011, pp. 410-419.
Schiraldi, C. et al., "Production of chondroitin sulfate and chondroitin," Applied Microbiology and Biotechnology, vol. 87, No. 4, 2010, pp. 1209-1220.
Tsutsumi, K. et al., "Functional expression and genomic structure of human chondroitin 6 sulfotransferase," FEBS Letters, vol. 441, No. 2, 1998, p. 235-241.
Uchimura, K. et al., "Mouse chondroitin 6-sulfotransferase: molecular cloning, characterization and chromosomal mapping," Glycobiology, vol. 8, No. 5, 1998, pp. 489-496.
Volpi, Nicola, Quality of Different Chondroitin Sulfate Preparations in Relation to their Therapeutic Activity, Journal of Pharmacy and Pharmacology, 2009, 1271-1280, vol. 61.
Volpi, Nicola, Analytical Aspects of Pharmaceutical Grade Chondroitin Sulfates, Journal of Pharmaceutical Sciences, Dec. 2007, 3168-3180, vol. 96, Issue 12.
Mucci, A. et al., 1H and 13C Nuclear Magnetic Resonance Identification and Characterization of Components of Chondroitin Sulfates of Various Origin, Carbohydrate Polymers, 2000, 37-45, vol. 41., Elsevier Science, Ltd.
Volpi, Nicola, Hyaluronic Acid and Chondroitin Sulfate Unsaturated Disaccharides Analysis by High-Performance Liquid Chromatography and Fluorimetric Detection with Dansylhydrazine, Analytical Biochemistry, 2000, 19-24, vol. 277, Academic Press.
Volpi, Nicola, Influence of Charge Density, Sulfate Group Position and Molecular Mass on Adsorption of Chondroitin Sulfate onto Coral, Biomaterials, 2002, 3015-3022, vol. 23, Elsevier Science Ltd.
Volpi, Nicola et al., The Protective Effect on Cu2+ and AAPH-Mediated Oxidation of Human Low-Density Lipoproteins Depends on Glycosaminoglycan Structure, Biochimie, 1999, 955-963, vol. 81.
Volpi, Nicola, Adsorption of Glycosaminoglycans onto Coral—A New Possible Implant Biomaterials for Regeneration Therapy, Biomaterials, 1999, 1359-1363, vol. 20, Elsevier Science Ltd.
Suzuki, Sakaru et al., Formation of Three Types of Disulfated Disaccharides from Chondroitin Sulfates by Chondroitinase Digestion, The Journal of Biological Chemistry, 1968, 1543-1550, vol. 243, Issue 7.
Jordan, K.M. et al., EULAR Recommendations 2003: An Evidence Based Approach to the Management of Knee Osteoarthritis: Report of a Task Force of the Standing Committee for International Clinical Studies Including Therapeutic Trials (ESCISIT), Ann Rheum Dis, 2003, 1145-1155, vol. 62.

(Continued)

*Primary Examiner* — Wu-Cheng Winston Shen
*Assistant Examiner* — Everett White
(74) *Attorney, Agent, or Firm* — Amin Talati, LLC; George M. Carrera, Jr.; Brent A. Batzer

(57) ABSTRACT

The present invention provides a shark-like chondroitin sulphate and a process for the preparation thereof. In particular, the present invention relates to a shark-like chondroitin sulphate, having a very low amount of 4-sulphate, a high charge density and a biological activity comparable to natural chondroitin sulphates. The invention also relates to a process for the preparation of said shark-like chondroitin sulphate affording substantially higher productivities and better reproducibility of product quality. The shark-like chondroitin sulphate of the invention shows a high molecular mass and its in vitro biological and anti-inflammatory effectiveness has been shown to be comparable to that of natural products making this polysaccharide potentially useful as a drug in pharmaceutical preparations and nutraceuticals.

18 Claims, 1 Drawing Sheet

(56) References Cited

OTHER PUBLICATIONS

Zhang, W. et al., EULAR Evidence Based Recommendations for the Management of Hand Osteoarthritis: Report of a Task Force of the EULAR Standing Committee for International Clinical Studies Including Therapeutics (ESCISIT), Ann Rheum Dis, 2007, 377-388, vol. 66.

McAlindon, T.E. et al., Glucosamine and Chondroitin for Treatment of Osteoarthritis: A Systematic Quality Assessment and Meta-Analysis, Journal of the American Medical Association, 2000, 1469-1475, vol. 283, Issue 11.

Volpi, Nicola et al., Quantitative and Qualitative Evaluation of Chondroitin Sulfate in Dietary Supplements, Food Anal. Methods, 2008, 195-204, vol. 1.

Volpi, Nicola et al., Two Analytical Approaches to the Evaluation of Chondroitin Sulfate in European Food Supplements, Separation Science, 2009, 3-8, vol. 1, Issue 1.

Ronca, Francesca et al., Anti-Inflammatory Activity of Chondroitin Sulfate, Osteoarthritis and Cartilage, 1998, 14-21, vol. 6, Supplement A.

Egea, J. et al., Antioxidant, Antiinflammatory and Neuroprotective Actions of Chondroitin Sulfate and Proteoglycans, Osteoarthritis and Cartilage, 2010, S24-S27, vol. 18.

Fuentes, Esteban P. et al., Oligosaccharide Mapping of Chondroitin Sulfate Obtained from Different Animal Sources, Acta Farm Bonaerense, 1998, 135-142, vol. 17, Issue 2.

Luo, X.M. et al., Chicken Keel Cartilage as a Source of Chondroitin Sulfate, Poultry Science, 2002, 1086-1089, vol. 81, Poultry Science Association, Inc.

Sugahara, Kazuyuki et al. Specificity Studies of Bacterial Sulfatases by Means of Structurally Defined Sulfated Oligosaccharides Isolated from Shark Cartilage Chondroitin Sulfate D, European Journal of Biochemistry, 1996, 865-870, vol. 239.

Lignot, B. et al., Enzymatic Extraction of Chondroitin Sulfate from Skate Cartilage and Concentration-Desalting by Ultrafiltration, Journal of Biotechnology, 2003, 281-284, vol. 103, Elseiver B.V.

\* cited by examiner

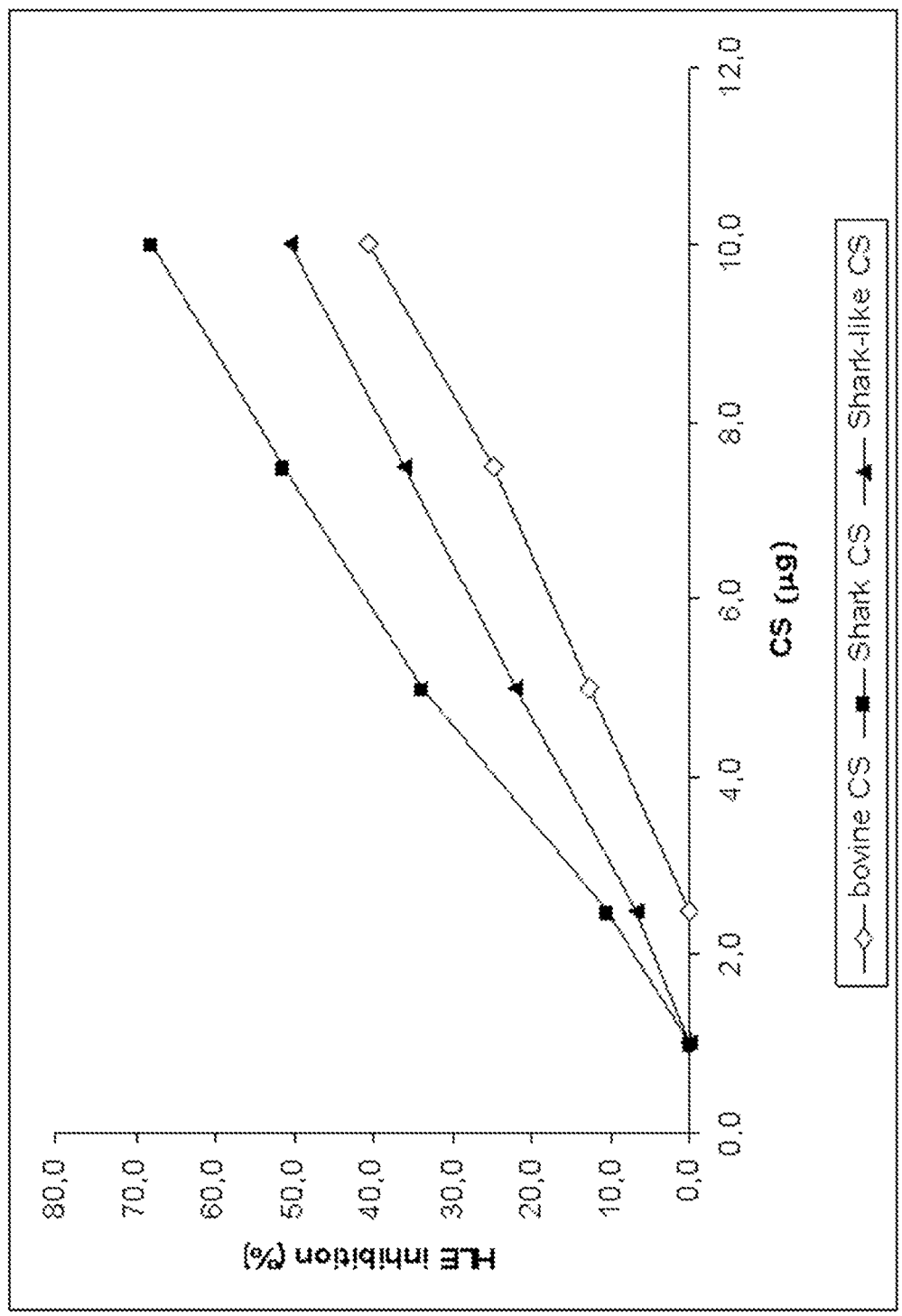

SHARK-LIKE CHONDROITIN SULPHATE AND PROCESS FOR THE PREPARATION THEREOF

The present invention concerns a shark-like chondroitin sulphate and a process for the preparation thereof. In particular, the present invention relates to a shark-like chondroitin sulphate, showing a very low amount of 4-sulphate, a high charge density and a biological activity comparable to natural chondroitin sulphates. The invention also relates to a process for the preparation of said shark-like chondroitin sulphate.

BACKGROUND

Chondroitin Sulphate (hereafter CS), belonging to the class of natural complex polysaccharides named glycosaminoglycans (GAGs), is composed of alternate disaccharide sequences of differently sulphated residues of D-glucuronic acid (GlcA) and of N-acetyl-D-galactosamine (GalNAc) linked by beta(1→3).

Depending on the disaccharide nature, CS with different carbohydrate backbones are known. In fact, even if both natural and synthetic known CS are mainly composed of various percentages of two kinds of disaccharide units, i.e., sulphated in position 4 or 6 of GalNAc, disaccharides with a different number and position of sulphate groups can be located, in various percentages, within the polysaccharide chains. For example, the unsulphated disaccharide is present, generally in low amounts, in the CS backbone, while disulphated disaccharides having two sulphate groups O-linked in various positions, such as position 2 of GlcA and position 6 of GalNAc (disaccharide D), or in position 4 and 6 of GalNAc (disaccharide E), may be present in the CS backbone in various percentages in relation to specific animal sources [Volpi, N., J Pharm Pharmacol 61, 1271, 2009 and Volpi, N., J Pharm Sci 96, 3168, 2007].

CS shows a disaccharide repeating unit having the following structural formula:

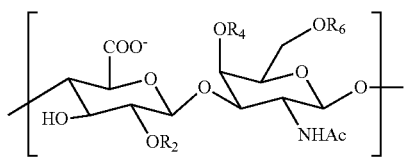

wherein $R_2$, $R_4$ and $R_6$ are independently either H or $SO_3^-$.

The meaning of some of the most recurring acronyms, currently used to briefly identify the differently sulphated residues of the alternate disaccharide sequences which make CS, are below reported.

| | |
|---|---|
| Di-0S | ($R_2$ = H; $R_4$ = H; $R_6$ = H) |
| Di-6S (C) | ($R_2$ = H; $R_4$ = H; $R_6$ = $SO_3^-$) |
| Di-4S (A) | ($R_2$ = H; $R_4$ = $SO_3^-$; $R_6$ = H) |
| Di-4,6diS (E) | ($R_2$ = H; $R_4$ = $SO_3^-$; $R_6$ = $SO_3^-$) |
| Di-2,6diS (D) | ($R_2$ = $SO_3^-$; R4 = H; $R_6$ = $SO_3^-$) |
| Di-2,4diS (B) | ($R_2$ = $SO_3^-$; R4 = $SO_3^-$; $R_6$ = H) |
| Di-2,4,6triS | ($R_2$ = $SO_3^-$; R4 = $SO_3^-$; $R_6$ = $SO_3^-$) |

Both natural and synthetic CS samples may be characterized and differentiated by means of sensitive, specific, validated and published analytical approaches, able to give CS structural characterization and parameters (for example specific sulphated groups, charge density, molecular mass, and purity) as well as biological activities.

Natural extractive CS samples may be characterized for structure and properties [Volpi, N., J Pharm Pharmacol 61, 1271, 2009; Volpi, N., J Pharm Sci 96, 3168, 2007; Mucci, A. et al., Carbohydr Polymers 41, 37, 2000; and Volpi, N., Analyt Biochem 277, 19, 2000].

As to the tri- and tetra-sulphated forms of CS ("triS" and "tetraS", respectively), it can be noted that they are not usually detected in natural extractive CS samples whereas they typically characterise synthetic CS; Di-2,4,6triS is taken as a standard in order to evaluate the presence of triS CS in synthetic CS products as the other theoretically possible triS forms are not present in the naturally derived products.

The following Table 1 illustrates the main disaccharides identified in natural CS samples extracted and purified from various organs and tissues, mainly cartilages.

TABLE 1

| | Bovine CS | Porcine CS | Chicken CS | Shark CS | Ray CS | Squid CS |
|---|---|---|---|---|---|---|
| Mn (kDa) | 12-17 | 9-14 | 8-13 | 25-40 | 27-34 | 60-80 |
| Mw (kDa) | 20-26 | 14-20 | 16-21 | 50-70 | 50-70 | 80-120 |
| Polydispersity Index | 1.8-2.2 | 1.4-1.8 | 1.6-2.0 | 1.0-2.0 | 1.2-2.5 | 0.8-1.3 |
| Di-0S | 6 | 6 | 8 | 3 | 3 | 13 |
| Di-6S (C) | 33 | 14 | 20 | 44 | 39 | 15 |
| Di-4S (A) | 61 | 80 | 72 | 32 | 43 | 50 |
| Di-2,6diS (D) | ND | ND | ND | 18 | 13 | 0 |
| Di-4,6diS (E) | ND | ND | ND | 2 | 1 | 22 |
| Di-2,4diS (B) | ND | ND | ND | 1 | 1 | 0 |
| triS | ND | ND | ND | ND | ND | ND |
| tetraS | ND | ND | ND | ND | ND | ND |

TABLE 1-continued

|  | Bovine CS | Porcine CS | Chicken CS | Shark CS | Ray CS | Squid CS |
|---|---|---|---|---|---|---|
| Charge Density | 0.90-0.96 | 0.92-0.96 | 0.90-0.94 | 1.15-1.25 | 1.08-1.20 | 1.00-1.20 |
| 4S/6S ratio | 1.50-2.00 | 4.50-7.00 | 3.00-4.00 | 0.45-0.90 | 1.00-1.40 | 2.50-4.00 |

Mn = number average molecular weight;
Mw = weight average molecular weight;
Polydispersity Index = Mw/Mn;
Charge Density is the number of sulfate groups per disaccharide units);
ND = Not Detected Table 1 illustrates the main structural parameters for the characterization of the principal natural CS samples purified from several sources.

In particular, molecular mass parameters are quite similar for terrestrial CS samples (bovine, porcine and chicken samples) but quite different from ichthyic samples (shark, ray and squid samples), the latter ones having molecular mass values greater than the former ones.

Furthermore, ichthyic CS samples have peculiar charge density values, greater than about 1.0, due to the presence of disulphated disaccharides and different from terrestrial samples having charge density values lower than about 1.0, due to the absence of disulphated disaccharides.

A further peculiarity of all natural CS is that when digested with chondroitinase ABC, a hydrolytic enzyme specific for either 4S or 6S sulphated disaccharides, as well as for unsulphated disaccharides, the polysaccharide chain is completely digested into disaccharide units. This can be easily observed with FACE (Fluorophore-Assisted Carbohydrate Electrophoresis) analysis. The complete digestion of natural CS is due to the absence of tri- and tetra-sulphated structures in the polysaccharide chain. Tri- and tetra-sulphated disaccharides, if present, are not recognised by chondroitinase ABC, not allowing a complete polysaccharide digestion, this produces partially undigested oligosaccharide chains easily determined in FACE analysis.

Finally, due to biosynthetic pathways, all known natural CS show the contemporary presence of disaccharides monosulphated in position 4 and position 6 of GalNAc (with the 4-sulphated disaccharide never lower than 30%), even if their ratio changes depending on the source.

As illustrated above, CS is a very complex heterogeneous macromolecule having variable structure and properties, depending on the extraction source.

Furthermore, as a result of the biosynthetic processes related to specific tissues and species, CS with different grades of polymerization may be biosynthesized producing macromolecules having various molecular masses and polydispersity.

Due to these structural variations, and in addition to the possible presence of specific oligosaccharide sequences, and purity of the preparations for therapy applications or in nutraceuticals, CS may have different properties and capacities.

In fact, different and peculiar activities have been reported depending on the CS structure [see, Volpi, N., Biomaterials 23, 3015, 2002; Volpi, N. et al., Biochimie 81, 955, 1999; Volpi, N., Biomaterials 20, 1359, 1999; and Suzuki, S. et al., J Biol Chem 243, 7, 1968].

Natural extractive CS is currently recommended by European League Against Rheumatism (EULAR) as a Symptomatic Slow Acting Drug for Osteo Arthritis (SYSADOA) in Europe in the treatment of knee OA [Jordan, K M et al., Ann Rheum Dis 62, 1145, 2003], hip [Jordan, K M et al., Ann Rheum Dis 62, 1145, 2003] and hand [Zhang, W. et al., Ann Rheum Dis 66, 377, 2007] based on research evidence and meta-analysis of numerous clinical studies.

Moreover, CS alone or in combination with other ingredients, is largely used as a nutraceutical, mostly in Europe and the United States [McAlindon, T E et al., JAMA 283, 1469, 2000. Volpi, N. et al., Food Anal Meth 1, 195, 2008. Volpi, N. et al., Separation Sc 1, 22, 2009].

CS effectiveness is strictly related to its anti-inflammatory activity, such as its ability to inhibit the activity of degradative enzymes as human leukocyte elastase (HLE) [Ronca, F. et al., Osteoarthritis Cartilage 6 Suppl A, 14, 1998. Egea, J. et al., Osteoarthritis Cartilage 18 Suppl 1, S24, 2010].

CS used worldwide in pharmaceutical or nutraceutical applications is obtained by extraction from tissues of several animals such as bovine and porcine [Fuentes, E P et al., Acta Farm Bonaerense 17, 135, 1998], avian [Luo, X M et al., Poult Sci 81, 1086-1089, 2002], cartilaginous fishes [Sugahara, K. et al., Eur J Biochem 239, 871, 1996. Lignot, B et al., J Biotechnol 103, 281, 2003], etc.

Yet, the animal origin of these products poses potential consumer safety problems associated with the possible presence of transmissible infective agents such as those causing spongiform encephalopathies in bovines, or due to a restriction in use related to religious issues.

In addition, the extractive nature of these products makes their supply potentially unreliable in view of a growing demand and increasing market volumes.

Such considerations have prompted the search for alternative, more dependable sources of CS, an example of which is the biotechnological production starting from the K4 capsular polysaccharide of E. coli as described in scientific and patent literature.

In this context, the term "biotechnological production" as used herein refers to a production method where a generally substantial portion of the final product is produced by a microorganism, or by isolated cells of a higher organism, in an artificial cultivation system, commonly and loosely referred to as "fermentation."

Basically, three major biotechnological production approaches have been used so far in the art.

The first one can be identified with the production of CS-like compounds using as the starting material the K4 capsular polysaccharide of E. coli O5:K4:H4, which is then subjected to chemical transformation, whereas the second approach can be seen as the direct biosynthesis of CS-like compounds by microorganisms and the third one recognised to be the biosynthetic production of unsulphated chondroitin followed by chemical or biochemical sulphation.

EP-A-1304338, belonging to the above first approach, describes the production of CS starting from the K4 polysaccharide produced in liquid cultures that is first extracted and purified, and subsequently re-dissolved and subjected to acid hydrolysis, the main effect of which is the removal of the fructose residues linked to the GlcA residues present in the linear polymer. A secondary effect is the partial hydrolysis of the polysaccharide chain, leading to lower molecular mass products. Subsequently, the de-fructosylated polymer that is identical to unsulphated chondroitin is variously sulphated at the C-4 or at the C-6 positions of the GalNAc residues by chemical means using appropriate protective groups at the 4 or 6 positions. Also, a CS is therein disclosed, at least 70% of its content consisting of mono- and/or di-sulphated in the 4 and 6 positions of the galactosamine moiety, the 2 position of the glucuronic moiety being unsulphated, having a Mw of 6-25 kDa and a carboxyl/sulphate group ratio (i.e. charge density) of 0.7-2.0.

WO 2009/149155, exemplifying the above second approach, describes the direct production of CS-like compounds by several microorganisms, both bacteria and fungi. A CS terrestrial-like compound is also therein disclosed, both the 4- and 6-positions of the galactosamine moiety being sulphated; the compound is reported to show a molecular weight (Mw) from about 300 Da to 35 kDa and a 4S/6S sulphate ratio ranging from lower than 1 to higher than 1.

The third of the above approaches includes several different strategies for the production of unsulphated chondroitin, the main of which are the enzymatic synthesis of the polymer in cell-free systems, like the ones disclosed for instance in EP-A-1950308 and EP-A-1964924, and the biosynthesis in recombinant cells obtained expressing into hosts capable of producing, from UDP-GlcA, the genes kfoA and kfoC extracted from *E. coli* K4 described, for instance, in WO 2008/133350.

Another example of biosynthetic production of unsulphated chondroitin is disclosed by the Italian patent application No. MI2010A001300 which, inter alia, relates to a method for the biotechnological production of chondroitin comprising cultivating in a suitable medium a recombinant microorganism, preferably *Escherichia coli* DSM23644, recovering and purifying the unsulphated chondroitin present in the microbial culture and subsequently chemically sulphating the latter.

A common feature of the processes for the production of CS described so far is a substantial reduction of the molecular mass of the original material both during the acid-catalyzed removal of the fructose residues and during the chemical synthesis steps required for the sulphation of GalNAc residues.

As an example, EP-A-1304338 describes a 6-25 kDa molecular mass CS while the molecular mass of the K4 polysaccharide, used as the starting material, is disclosed to be 150-400 kDa.

SUMMARY

The present invention provides a shark-like chondroitin sulphate and a process for the preparation thereof. In particular, the present invention relates to a shark-like chondroitin sulphate, showing a very low amount of 4-sulphate, a high charge density and a biological activity comparable to natural chondroitin sulphates.

In one embodiment, a shark-like chondroitin sulphate, free of tri-, tetra- and 2,4di-sulphated disaccharides, consisting of 60-99% of 6-sulphate, 0.5-30% of 2,6-disulphate, 0.1-5% of 4,6 disulphate, 0.1-5% of unsulphated chondroitin and 0.1-1% of 4-sulphate, all percentages being expressed with respect to the total disaccharide content of the shark-like chondroitin sulphate, the latter showing a number average molecular weight (Mn) of 40-85 kDa and a weight average molecular weight (Mw) of 50-95 kDa is disclosed.

Shark-like chondroitin sulphates in accordance with the invention have been found to have an in vitro biological and anti-inflammatory effectiveness comparable to the ones of natural products and certain embodiments can be used as a drug in pharmaceutical preparations and/or nutraceuticals. Accordingly, in another aspect, a therapeutically effective amount of a shark-like chondroitin sulphate in accordance with the invention can be administered to a subject in need thereof for the treatment or prevention of osteoarthritis, or for the maintenance of musculoskeletal health.

In another aspect, shark-like chondroitin sulphate can be prepared by salifying unsulphated chondroitin, as free acid, with a tetramethyl-, tetraethyl- and tetrabutyl-, ammonium or pyridinium salt; drying the salified unsulphated chondroitin, as free acid and/or sodium salt to reduce the water content; selectively sulphating the 6-position of the salified unsulphated chondroitin by adding sulphur trioxide pyridine complex or sulphur trioxide dimethylformamide complex; quenching the reaction, filtering, and concentrating to dryness the resulting solution to obtain a dried solid; dissolving the dried solid in an aqueous sodium chloride solution, ultrafiltrating and dialysing the resulting solution; recovering the product from the solution; purifying the product to obtain purified product in an acidic form or as the sodium salt thereof; and recovering the purified product.

BRIEF DESCRIPTION OF THE DRAWING

FIG. 1 is a graphical comparison of HLE Inhibition vs. CS concentration of a shark-like chondroitin sulphate in accordance with the invention to natural chondroitin sulphates.

DETAILED DESCRIPTION

A first aspect of the present invention is a shark-like chondroitin sulphate, free of tri-, tetra- and 2,4-di-sulphated disaccharides, consisting of 60-99% of 6-sulphate, 0.5-30% of 2,6-disulphate, 0.1-5% of 4,6 disulphate, 0.1-5% of unsulphated chondroitin and 0, 1-1% of 4-sulphate, all percentages being expressed with respect to the total disaccharide content of the shark-like chondroitin sulphate, the latter showing a number average molecular weight (Mn) of 40-85 kDa and a weight average molecular weight (Mw) of 50-95 kDa.

Preferably, the shark-like chondroitin sulphate of the present invention consists of 70-90% of 6-sulphate, 8.5-20% of 2,6-disulphate, 0.1-5% of 4,6 disulphate, 0.1-5% of unsulphated chondroitin and 0.1-1% of 4-sulphate, all percentages being expressed with respect to the total disaccharide content of the shark-like chondroitin sulphate, the latter showing a number average molecular weight (Mn) of 40-65 kDa and a weight average molecular weight (Mw) of 50-70 kDa.

The CS object of the present invention is characterized by a high-molecular mass and by peculiar and particular sulphated groups, mainly in position 6, as well as by a very small amount of 4-sulphated disaccharide.

Examining the features of the CS of the present invention and comparing them with the ones shown in the above Table 1 relating to natural extractive CS samples, it can be seen that the CS of the present invention approximately resembles to shark CS.

Also, the CS object of the present invention does not show any polysulphated disaccharides, and in particular it does not show either tri- or tetra-sulphated disaccharides typically characterising the CS obtained by the synthetic methods disclosed in the prior art and detectable, after digestion with chondroitinase ABC, as a non-degraded product.

Further, the CS object of the present invention is highly purified (on the basis of the amount of non-degraded product after digestion with chondroitinase ABC) and can be clearly distinguished over the CS disclosed in EP-A-1304338 having a molecular mass of 6-25 kDa and a high amount of unsulphated chondroitin (>10%) and a broad range of charge density (0.7-2), whereas, in distinct contrast, the ranges of the charge density of the CS of the invention are narrower and preferably amounting to 1.05-1.30.

Both Mn and Mw can be calculated according to the common methods known to a person skilled in the art; for instance High-Performance Size-Exclusion Chromatography (HPSEC); preferably, Mn and Mw can be determined by HPSEC, equipped with integrated specialized software for Gel Permeation Chromatography (GPC).

Preferably, the sum of 2,6-disulphate and 4,6-disulphate in the CS of the present invention amounts to 10-25% of the total disaccharide content.

According to another aspect, the present invention relates to a composition comprising the shark-like chondroitin sulphate of the present invention and a pharmaceutically or nutraceutically acceptable carrier such as, for instance, microcrystalline cellulose, dextrin, maltodextrin, cyclodextrin, sulfobutylether beta-cyclodextrin, soy lecithin, palmitoleic acid, liposomes, sucresters, and the like.

As the skilled person will understand on the basis of the common general knowledge of the field, the composition of the invention may be formulated in various forms, either solid (e.g., tablets, hard capsules, soft gel capsules) or liquid (e.g., solutions or powdered drink mixes), preferably in the form of a parenteral and/or oral pharmaceutical and/or nutraceutical preparation, and may further include other inactive and/or active ingredients.

Among such further ingredients, the composition of the invention may also and preferably include at least one of the following substances: glucosamine hydrochloride, glucosamine sulphate, N-acetyl glucosamine, hyaluronic acid, heparin, keratin, dermatin, methylsulphonylmethane, folates or reduced folates, B-group vitamins, S-adenosylmethionine (SAMe), ascorbic acid or manganese ascorbate, and may be administered in an effective amount to a subject in the need thereof, depending on the needs and circumstances the case may require.

By mere way of example, the shark-like CS and/or the composition of the present invention may be administered to a subject in an amount of 100-3000 mg/day, preferably an amount of 1000-2000 mg/day, more preferably an amount of 1200-1800 mg/day, generally divided in two/three doses per day.

According to another aspect, the present invention relates to the shark-like chondroitin sulphate or the composition of the present invention, for use in the prevention or treatment of osteoarthritis, or for the maintenance of musculoskeletal health, for example, as an active ingredient in either a drug or a food additive or a nutritional supplement.

By mere way of example, the shark-like CS or the composition of the present invention, as above defined, may be used for the preparation of a medicament, a food additive or a nutritional supplement, for the prevention and/or the treatment of hip, hand and knee osteoarthritis (OA) and its main symptoms such as pain, joint swelling, inflammation, Alzheimer's disease, microbial infections, arteriosclerosis, osteoporosis and as an adjuvant in cancer therapy and tissue regeneration, including nerve tissue regeneration.

According to still another aspect, the present invention concerns a process for preparing the above defined shark-like chondroitin, comprising:

a) salifying unsulphated chondroitin, as free acid, previously dissolved in an aqueous environment, with a salt selected from the group consisting of tetramethyl-, tetraethyl- and tetrabutyl-, ammonium or pyridinium;

b) drying the salified unsulphated chondroitin resulting from step a) to 5-15% of water content;

c) drying the salified unsulphated chondroitin resulting from step b), at a temperature of 100° C.-170° C., to 0.1-3% of water content;

d) selectively sulphating the 6-position of the salified unsulphated chondroitin resulting from step c), solubilized in N-methylpyrrolidone or dimethylformamide, at a temperature of 0° C.-30° C., by adding 1-2 equivalents of sulphur trioxide pyridine complex or sulphur trioxide dimethylformamide complex, at time intervals of 1-3 hours, to a total of 2-15 equivalents of sulphur trioxide pyridine complex or sulphur trioxide dimethylformamide complex, is added; leaving the resulting solution under stirring for 2-24 h;

e) quenching the reaction carried out in step d) with an aqueous sodium bicarbonate or carbonate solution, filtering and concentrating to dryness the resulting solution to obtain a dried solid;

f) dissolving the dried solid in an aqueous sodium chloride solution, ultrafiltrating and dialysing the resulting solution;

g) recovering the product from the solution resulting from step f);

h) purifying the product resulting from step g) and obtaining the latter either in acidic form or as the sodium salt thereof; and i) recovering the product resulting from step h).

The salification of unsulphated chondroitin in step a) is preferably carried out with a salt selected from the group consisting of tetramethyl-, tetraethyl- and tetrabutyl-ammonium, most preferably with tetrabutyl ammonium whereas the drying of the unsulphated chondroitin in step b) may be carried out by freeze-drying or spray-drying.

The drying of the unsulphated chondroitin salt in step c) is preferably carried out till 0.5-2% of water whereas the solubilization of the unsulphated chondroitin salt resulting from said step is preferably carried out in dimethylformamide.

The selective sulphating in step d) is preferably carried out adding a total of 6-12, more preferably 6-9, equivalents of sulphur trioxide pyridine complex.

Alternatively, when the selective sulphating in step d) is carried out by sulphur trioxide dimethylformamide complex, a total of 1-9, preferably 2-4, equivalents are added.

Further, the selective sulphating in step d) is preferably carried out at a temperature of 10° C.-20° C. whereas, at the end of step d), the resulting solution is preferably left under stirring for 2-6 h.

According to still another preferred embodiment of the process of the invention, the product from the solution resulting from step f) is recovered by freeze-drying, spray-drying or precipitation in an alcoholic environment.

The process for preparing the shark-like chondroitin as described above allows maintaining unchanged the molecular weight of the native polysaccharide.

Surprisingly, the process of the invention allows one to avoid carrying out any step aiming at protecting any of the secondary hydroxyl groups, likely because the reactivity of the primary hydroxyl groups in the 6-position of GalNAc guarantees the selectivity of the reaction.

Besides, the process of the invention allows one to get substantially higher productivity and better reproducibility of the quality of the product in comparison with the prior art; for instance, in respect with EP-A-1304388, where the sulphating steps result in a broader range of carboxyl/sulphate group ratio, amounting to 0.7-2.0.

Also, the process of the invention allows getting a product showing very low amounts of 4-sulphated disaccharide and substantially free of polysulphated disaccharides; in particular, it allows getting a product free from either triS or tetraS saccharides.

Typically, the process for preparing the shark-like chondroitin as described above can be carried out by dissolving unsulphated chondroitin, as free acid or sodium salt, prepared for instance by defructosilating the K4 capsular polymer obtained by fermentation, as described by Manzoni (Biotechnology Letters 18, 383-6, 1996) and Rodriguez (Eur. J. of Biochem 177, 117-24, 1988), in an aqueous environment.

In case the unsulphated chondroitin is under the form of its sodium salt, after its complete dissolution, the resulting solution is eluted, conveniently at a temperature of 0° C.-30° C., in a column containing a cationic exchange resin (such as, for instance, Amberjet 1200 H, available from the Rohm and Haas Company, and the like) collecting the eluted portions conveniently at a pH of 1.5-4.0, preferably 1.5-3.0, and recovering the aqueous acid portions.

Alternatively, this step can be carried out in batch: after dissolution of the unsulphated chondroitin sodium salt in water, which is preferably obtained by stirring 20-60 min at 0° C.-30° C., the cationic resin (Amberjet 1200 H, available from the Rohm and Haas Company, and the like) is added thereto, the pH of the solution after the resin addition resulting to be between 1.5 and 3.0. The solution is then filtered and the resulting acidic filtrate is collected.

The acid solution of the unsulphated chondroitin, obtained either directly dissolving the unsulphated chondroitin as free acid or purifying its sodium salt solution as above described, either in continuous or in batch, is then added with an aqueous solution of an ion selected from the group consisting of tetramethyl-, tetraethyl- and tetrabutyl-, ammonium or pyridinium, conveniently till a pH of 6.0-8.0, preferably 6.0-7.0, the solution is evaporated to dryness, for instance by freeze-drying or spray-drying, to 5-15% of water content, so to recover the corresponding chondroitin salt.

The resulting chondroitin salt is then subjected to a second drying step, at a temperature of 100° C.-170° C., to 0.1-3% of water content, so to finally recover the corresponding unsulphated chondroitin salt.

The corresponding unsulphated chondroitin salt, obtained as above described, is then selectively sulphated in the 6-position, with no need of protecting any of the functional moieties, by solubilizing it in a solvent selected from N-methylpyrrolidone or dimethylformamide, at a temperature of 0° C.-30° C., preferably 10° C.-20° C., conveniently eluting the completely dissolved unsulphated chondroitin salt in a column containing a cationic exchange resin (such as, for instance, Amberjet 1200 H, available from Rohm and Haas, and the like), by adding 1-2 equivalents of sulphur trioxide pyridine complex or sulphur trioxide dimethylformamide complex, at time intervals of 1-3 hours, until a total of 2-15 equivalents of pyridine or dimethylformamide sulphur trioxide complex is added, leaving the resulting solution under stirring for 2-24 h, preferably 2-6 h.

The resulting reaction mass is thereafter quenched in an aqueous sodium bicarbonate or carbonate solution and then recovered, for instance by treatment with sodium bicarbonate and filtration of the resulting insoluble salts, evaporated to dryness and again dissolved in an aqueous sodium chloride solution, recovered and finally treated, for instance by ultrafiltration and dialysis, so to remove the remaining salts and low molecular weight impurities and finally recovering the product, for instance, by freeze-drying, spray-drying or precipitation in an alcoholic environment.

The resulting chondroitin 6-sulphate obtained as illustrated above is then purified, for example by cationic exchange resin column chromatography, so to obtain it in its acid form, and alternatively subsequently obtained as the sodium salt thereof by adding, for instance, sodium hydroxide.

The chondroitin 6-sulphate so obtained is finally recovered, for example drying it in an oven, under vacuum, at 50° C.-70° C. or chromatographically purified, obtaining a shark-like chondroitin sulphate, free of tri-, tetra- and 2,4di-sulphated disaccharides, showing a Mn of 40-85 kDa, a Mw of 50-95 kDa.

The following examples illustrate the invention.

EXAMPLE 1

Salification 20 g of chondroitin sodium salt, prepared by defructosilating the K4 capsular polymer obtained by fermentation as described by Manzoni (Biotechnology Letters 18, 383-6, 1996) and Rodriguez (Eur. J. of Biochem 177, 117-24, 1998) were dissolved in demineralised water (500 ml). After complete dissolution, the resulting solution was eluted at 5° C. in a column containing a cationic exchange resin (160 ml of Amberjet 1200 H, available from the Rohm and Haas Company), previously hydrated and prepared in acid form. The eluted portions were recovered at a pH of 1.9, collecting the aqueous acid portions and adding thereto a 16% aqueous solution of tetrabutyl ammonium, to a pH of 7.0; and the solution was then evaporated to dryness by freeze-drying so to recover 20.8 g of chondroitin as tetrabutyl ammonium salt.

The resulting salt was then subjected to a second thermal treatment in a static dryer at 105° C. for 4 h, under vacuum, to a residual humidity of less than 0.2%. 18.5 g of chondroitin as tetrabutyl ammonium salt were thus obtained.

EXAMPLE 2

Salification 12 g of unsulphated chondroitin prepared by defructosilating the K4 capsular polymer obtained by fermentation as described by Manzoni (Biotechnology Letters 18, 383-6, 1996) and Rodriguez (Eur. J. of Biochem 177, 117-24, 1998) were dissolved in 20 ml of demineralised water and, after having acidified till pH 2.5 by 1M HCl and added 80 ml of ethanol, unsulphated chondroitin was precipitated as free acid.

After filtering and washing with ethanol, 10.3 g of the product were obtained as a white solid that, after having been dried under vacuum at 50° C., showed an acid titre of 90% calculated on the product per se and contained 8% of residual water.

The resulting solid was suspended in 20 ml of water and added with a 40% w/w aqueous solution of tetrabutyl ammonium hydroxide till pH 8. The resulting solution was then freeze-dried till 2.5% residual water, so to obtain 15.9 g of solid chondroitin as tetrabutyl ammonium salt.

The resulting salt was then subject to a second thermal treatment in a static dryer at 105° C. for 4 h, under vacuum, to a residual humidity of less than 0.2%. 15.4 g of tetrabutyl chondroitin were thus obtained.

EXAMPLE 3

Sulphation 1.4 g of tetrabutyl chondroitin obtained as illustrated in Example 1 and 84 ml of DMF were charged in a 250 ml four-neck flask kept under an inert atmosphere ($N_2$), mechanical stirring and in the presence of a bubble cooling system, calcium chloride trap and thermometer.

The resulting suspension was left under stirring till complete dissolution, subsequently adjusting the temperature at 23° C.

Once the temperature was adjusted, solid sulphur trioxide pyridine complex was added portion-wise (1.07 g, 3 eq) to the solution, keeping the reaction under stirring for 1 h and then adding further solid sulphur trioxide pyridine complex (1.07 g; 3 eq). After a further 1 h stirring at the same temperature, the reaction mixture was transferred in a 500 ml flask, containing a saturated solution of sodium hydrogencarbonate and cooled at 10° C.

After having left the temperature raise up to 20° C., filtering on a Buchner funnel was carried out, recovering the filtrate and evaporating it to dryness under vacuum.

The resulting dried solid (2.3 g) was finely milled and redissolved in a 0.3M NaCl solution (130 ml), subjecting the solution so obtained to ultrafiltering using a 3 kDa cut-off membrane and maintaining the pH of the retentate at 7.0. The ultrafiltered solution was then dialysed for removing salts, recovering the product by lyophilisation.

The resulting product was finally dried at 50° C. and 10 mbar, until 1 g of substance was obtained, showing a titre (calculated by determining glucuronic acid-Pulsed Amperometric Detection "PAD") of 95%, a Mn of 60 kDa and a Mw of 67.3 kDa, determined by High-performance size-exclusion chromatography (HPSEC) equipped with integrated specialized software for GPC.

EXAMPLE 4

Sulphation 1.21 g of chondroitin as tetrabutyl ammonium salt, obtained as illustrated in Example 1, and 72 ml of DMF were charged in a 250 ml four-neck flask kept under an inert atmosphere ($N_2$), mechanical stirring and in the presence of a bubble cooling system, calcium chloride trap and thermometer.

The resulting suspension was left under stirring until complete dissolution, subsequently adjusting the temperature at 10° C.

Once the temperature was adjusted, solid sulphur trioxide DMF complex was added (0.88 g, 3 eq) to the solution, keeping the reaction under stirring for 1 h. Sodium hydrogencarbonate (0.97 g, 6 eq) was added keeping the same temperature and the stirring was continued for 1 h having left the temperature raise up to 20° C. The resulting suspension was filtered on a Buchner funnel and the recovered filtrate was evaporated to dryness under vacuum.

The resulting dried solid (2.05 g) was finely milled and redissolved in a 0.3M NaCl solution (130 ml), subjecting the solution so obtained to ultrafiltering using a 3 kDa cut-off membrane and maintaining the pH of the retentate at 7.0. The ultrafiltered solution was then dialysed for removing salts, recovering the product by lyophilisation.

The resulting product was finally dried at 50° C. and 10 mbar, till 0.95 g of substance was obtained, showing a titre (calculated by determining glucuronic acid-PAD) of 94%, a Mn of 62 kDa and a Mw of 68.3 kDa, determined by High-performance size-exclusion chromatography (HPSEC) equipped with integrated specialized software for GPC.

EXAMPLE 5

Analysis of chondroitin 6-sulphate

The composition of the CS obtained from Examples 3 and 4, was studied by HPLC of the digestion products thereof by treating the CS obtained as above described with chondroitinase ABC, according to the method disclosed by Sim, Joon-Soo et al. (J. Chromatography B, 2005 vol. 818, pages 133-139).

The analysis was carried out by using a column HPLC-SAX, 250×4.6 mm 10 μm, eluting with gradient, starting from 3.5 mM HCl (pH=3.5) (100%) initial phase till a concentration equal to 1M NaCl in HC13.5 mM (pH=3.5) (100%).

The same products resulting from the digestion with chondroitinase ABC were analysed in FACE (Fluorophore-Assisted Carbohydrate Electrophoresis) analysis in order to point out the presence of non digested polysaccharide. The results show a digestion rate over 95%. The high digestion rate indicates the substantial absence of tri- and/or tetra-sulphate disaccharides in the structure of the CS obtained.

The following Table 2 shows the main disaccharides identified for the products prepared in Examples 3 and 4.

TABLE 2

|  | CS (Example 3) | CS (Example 4) |
|---|---|---|
| Molecular mass: |  |  |
| Mn (kDa) | 55.2 | 62 |
| Mw (kDa) | 67.3 | 68.3 |
| Polydispersity | 1.2 | 1.2 |
| Disaccharides: |  |  |
| Di-0S | 3.5 | 2.8 |
| Di-6S | 72.1 | 83.1 |
| Di-4S | 0.1 | 0.2 |
| Di-2,6diS | 18.9 | 13.8 |
| Di-4,6diS | 3.5 | 0.1 |
| Di-2,4diS | ND | ND |
| triS | ND | ND |
| tetraS | ND | ND |
| Charge Density | 1.21 | 1.10 |

Mn = number average molecular weight;
Mw = weight average molecular weight;
Polydispersity Index = Mw/Mn;
Charge Density is the number of sulfate groups per disaccharide units);
ND = Not Detected By comparing the above Table 2 with Table 1, it can be seen that the composition of the CS object of the present invention shows to closely relate to shark CS, since the former shows very low amounts of Di-4S and is mostly composed of Di-6S whereas Di-0S, Di-2,6diS and Di-4,6diS resulted to be approximately superimposable with the values reported for shark CS; further the CS of the present invention showed a charge density greater than 1.0. Also, the products obtained carrying out both Example 3 and 4 showed neither triS nor tetraS forms of CS.

Besides, the CS object of the present invention shows a peculiar and particular sulphate content when compared to some of the products disclosed in the prior art, as illustrated in the following Table 3.

TABLE 3

|  | Di-0S | Di-4S | Di-6S | Di-4,6diS | Di-2,6diS |
|---|---|---|---|---|---|
| EP-A-1304388 | YES | YES | YES | YES | NO |
| WO 2009/149155 | NO | YES | YES | NO | NO |
| EP-A-1964924 | YES | NO | NO | NO | NO |
| EP-A-1950308 | YES | NO | NO | NO | NO |
| MI2010A001300 | YES | NO | NO | NO | NO |
| Shark-like CS (Example 3) | YES | YES | YES | YES | YES |
| Shark-like CS (Example 4) | YES | YES | YES | YES | YES |

EXAMPLE 6

As CS effectiveness is strictly related to its anti-inflammatory activity, such as its ability to inhibit the activity of degradative enzymes as human leukocyte elastase (HLE), the CS object of the present invention was tested in vitro for its ability to inhibit such activity of HLE and compared to bovine CS (1$^{st}$ European Pharmacopoeia CS Standard) and CS extracted from shark cartilages samples.

The comparative results are shown in FIG. 1.

A sample of shark-like CS according to the present invention, as obtained according to the procedure described in Example 3, was compared with bovine CS (1$^{st}$ European Pharmacopoeia CS Standard) sold by Bioiberica and CS extracted from shark cartilages.

The elastase activity was determined by spectrophotometric assay by using a chromogenic artificial substrate (N-Succinyl-Ala-Ala-Ala-p-nitroanilide) specific for HLE. After preincubation of the enzyme with increasing amounts of CS, the activity was determined by incubation with chromogenic substrate (N-Succinyl-Ala-Ala-Ala-p-nitroanilide). After stopping the reaction, the resulting product was quantitatively determined by spectrophotometric evaluation.

TABLE 4

| | HLE Inhibition (%) | | |
|---|---|---|---|
| μg | bovine CS (comparative) | shark CS (comparative) | shark-like CS (invention) |
| 1.0 | 0.0 | 0.0 | 0.0 |
| 2.5 | 0.0 | 10.5 | 6.7 |
| 5.0 | 12.8 | 33.7 | 21.9 |
| 7.5 | 24.9 | 51.4 | 36.1 |
| 10.0 | 40.6 | 68.0 | 50.3 |

FIG. 1 illustrates the data reported in Table 4 and shows that the shark-like CS of the present invention is able to meaningfully inhibit the human leukocyte elastase activity, in an effective manner, comparable to the one shown by the natural CS samples.

The biological activity and anti-inflammatory properties shown in vitro by the CS object of the present invention make the latter comparable to natural products and therefore potentially useful as a drug in pharmaceutical preparations and nutraceuticals.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

The invention claimed is:

1. A chondroitin sulphate, free of tri-, tetra and 2,4-disulphated disaccharides, consisting of 60-99% of 6-sulphate, 0.5-30% of 2,6-disulphate, 0.1-5% of 4,6-disulphate, 0.1-5% of unsulphated chondroitin and 0.1-1% of 4-sulphate, all percentages being expressed with respect to a total disaccharide content of the chondroitin sulphate, the chondroitin sulphate having a number average molecular weight (Mn) of 40-85 kDa and a weight average molecular weight (Mw) of 50-95 kDa.

2. The chondroitin sulphate according to claim 1, consisting of 70-90% of 6-sulphate, 8.5-20% of 2,6-disulphate, 0.1-5% of 4,6 disulphate, 0.1-5% of unsulphated chondroitin and 0.1-1% of 4-sulphate, all percentages being expressed with respect to the total disaccharide content of the chondroitin sulphate, the chondroitin sulphate having a number average molecular weight (Mn) of 40-65 kDa and a weight average molecular weight (Mw) of 50-70 kDa.

3. The chondroitin sulphate according to claim 1, wherein the sum of 2,6-disulphate and 4,6 disulphate amounts to 10-25% of the total disaccharide content.

4. A composition comprising the chondroitin sulphate according to claim 1 and a pharmaceutically or nutraceutically acceptable carrier.

5. A process for preparing the chondroitin sulphate according to claim 1, comprising:
   a) salifying unsulphated chondroitin, as free acid, previously dissolved in an aqueous environment, with a salt selected from the group consisting of tetramethyl-, tetraethyland tetrabutyl-, ammonium or pyridinium;
   b) drying the salified unsulphated chondroitin, as free acid and/or sodium salt, resulting from step a) to 5-15% of water content;
   c) drying the salified unsulphated chondroitin resulting from step b), at a temperature of 100° C.-170° C., to 0.1-3% of water content;
   d) selectively sulphating the 6-position of the salified unsulphated chondroitin resulting from step c), solubilized in N-methyl pyrrolidone or dimethylformamide, at a temperature of 0° C.-30° C., by adding 1-2 equivalents of sulphur trioxide pyridine complex or sulphur trioxide dimethylformamide complex, at time intervals of 1-3 hours, until a total of 2-15 equivalents of sulphur trioxide pyridine complex or sulphur trioxide dimethylformamide complex, is added; leaving the resulting solution under stirring for 2-24h;
   e) quenching the reaction carried out in step d) with an aqueous sodium bicarbonate or carbonate solution, filtering and concentrating to dryness the resulting solution to obtain a dried solid;
   f) dissolving the dried solid in an aqueous sodium chloride solution, ultrafiltrating and dialysing the resulting solution;
   g) recovering the product from the solution resulting from step f);
   h) purifying the product resulting from step g) and obtaining the latter either in acidic form or as the sodium salt thereof; and
   i) recovering the product resulting from step h).

6. The process according to claim 5, wherein the salification of unsulphated chondroitin in step a) is carried out with a salt selected from the group consisting of tetramethyl-, tetraethyl- and tetrabutyl- ammonium.

7. The process according to claim 5, wherein the salification of the unsulphated chondroitin in step a) is carried out with tetrabutyl ammonium.

8. The process according to claim 5, wherein the drying of the unsulphated chondroitin in step b) is carried out by freeze-drying or spray-drying.

9. The process according to claim 5, wherein the drying of the unsulphated chondroitin salt in step c) is carried out till 0.5-2% of water.

10. The process according to claim 5, wherein the solubilization of the unsulphated chondroitin salt resulting from step c) is carried out in dimethylformamide.

11. The process according to claim 5, wherein the selective sulphating in step d) is carried out by adding a total of 6-12 equivalents of sulphur trioxide pyridine complex.

12. The process according to claim 5, wherein the selective sulphating in step d) is carried out by adding a total of 6-9 equivalents of sulphur trioxide pyridine complex.

13. The process according to claim 5, wherein the selective sulphating in step d) is carried out by adding a total of 1-9 equivalents of sulphur trioxide dimethylformamide complex.

14. The process according to claim 5, wherein the selective sulphating in step d) is carried out by adding a total of 2-4 equivalents of sulphur trioxide dimethylformamide complex.

15. The process according to claim 5, wherein the selective sulphating in step d) is carried out at a temperature of 10° C.-20° C.

16. The process according to claim 5, wherein at the end of step d) the resulting solution is left under stirring for 2-6h.

17. The process according to claim 5, wherein in step g) the product is recovered by freeze-drying, spray-drying or precipitation in an alcoholic environment.

18. A method for the treatment of osteoarthritis, or for the maintenance of musculoskeletal health, comprising administering to a patient in need thereof a therapeutically effective amount of a chondroitin sulphate or a composition comprising a chondroitin sulphate according to claim 1.

\* \* \* \* \*